(12) United States Patent
Merson et al.

(10) Patent No.: US 11,464,910 B1
(45) Date of Patent: Oct. 11, 2022

(54) SYRINGE CONTROL STRUCTURE AND MANUFACTURE METHOD

(71) Applicants: Alexander Merson, Brooklyn, NY (US); Gennady I Kleyman, Brooklyn, NY (US)

(72) Inventors: Alexander Merson, Brooklyn, NY (US); Gennady I Kleyman, Brooklyn, NY (US)

(73) Assignee: Alger & Klemer, Brooklyn, NY (US)

( * ) Notice: Subject to any disclaimer, the term of this patent is extended or adjusted under 35 U.S.C. 154(b) by 118 days.

(21) Appl. No.: 16/999,788

(22) Filed: Aug. 21, 2020

(51) Int. Cl.
*A61M 5/31* (2006.01)
*A61M 5/315* (2006.01)

(52) U.S. Cl.
CPC ...... *A61M 5/3137* (2013.01); *A61M 5/31511* (2013.01); *A61M 5/31576* (2013.01); *A61M 2005/3139* (2013.01)

(58) Field of Classification Search
CPC ............ A61M 5/3137; A61M 5/31511; A61M 5/31576; A61M 2005/3139; A61M 5/3148
See application file for complete search history.

(56) References Cited

U.S. PATENT DOCUMENTS

| | | | |
|---|---|---|---|
| 2,842,128 A * | 7/1958 | Hein, Jr. | A61M 5/31 604/227 |
| 3,316,909 A | 5/1967 | Cowley | |
| 4,217,896 A | 8/1980 | Behnke | |
| 5,833,668 A * | 11/1998 | Aguilar | A61M 5/3135 604/227 |
| 6,231,550 B1 | 5/2001 | Laughlin | |
| 6,669,672 B2 | 12/2003 | Wu | |
| 9,067,023 B2 | 6/2015 | Bertucci | |
| 10,980,945 B1 * | 4/2021 | Patron Borbolla | A61M 5/3137 |
| 2005/0209571 A1 | 9/2005 | McKay | |
| 2007/0208310 A1 * | 9/2007 | Stadick | A61M 5/3148 604/187 |
| 2012/0220948 A1 | 8/2012 | Barbour | |
| 2020/0206425 A1 * | 7/2020 | Keating | A61M 5/3135 |

\* cited by examiner

*Primary Examiner* — Bhisma Mehta
*Assistant Examiner* — Hong-Van N Trinh (57) ABSTRACT

An improved hypodermic syringe including finger-holding surfaces that substantially or completely surround the operator finger and include an interior tapered portion to better engage a finger, which facilitates one-handed use by allowing the same hand that holds the syringe to operate the plunger conveniently to accomplish both the distal (injecting) stroke and the proximal (aspirating) stroke.

2 Claims, 11 Drawing Sheets

SYRINGE CONTROL STRUCTURE AND MANUFACTURE METHOD

FIELD OF THE INVENTION

The present invention relates to hypodermic syringes structured to facilitate use, in particular, hypodermic syringes having finger receptacles to better engage operator fingers to facilitate single-hand use of the hypodermic syringe.

BACKGROUND OF THE INVENTION

Hypodermic used requires skilled and confident, accurate operation (e.g. a controlled compression of a syringe plunger) and simultaneous precise control of the needle location and depth. Moreover, it is very important to precisely accomplish both the distal (injecting) stroke, e.g. to determine whether the needle is in a blood vessel, and the proximal (aspirating) stroke. Existing syringes typically have limited plunger and barrel body surfaces used to grasp, operate and control dispensing of the syringe content, which syringe surfaces typically minimally accommodate the diverse finger sizes, or have any structure to enhance the operation and control of the syringe by the user.

SUMMARY OF THE INVENTION

Disclosed is an ergonomically improved hypodermic syringe including finger-holding surfaces that substantially or completely surround the operator finger and include an interior tapered portion to better engage a finger, which facilitates one-handed use by allowing the same hand that holds the syringe to operate the plunger conveniently to accomplish both the distal (injecting) stroke and the proximal (aspirating) stroke.

One embodiment includes a ring grip on the operating (finger) end of the syringe plunger, sized and shaped to accommodate or adjust for a snug fit with fingers and thumbs of varying sizes and additional finger holding structure located on the syringe barrel that can accommodate or adjust for a snug fit with index and middle fingers. Another embodiment includes structures that adjust to reduce the space between the grip and better engage the operator finger. Other embodiments apply similar structural improvement to finger grip(s) on the syringe barrel, and separate similarly shaped finger grips that may be added or attached to an existing syringe plunger and barrel.

These embodiments make the syringe significantly more easy, predictable, and controllable to use with one hand. The result is a syringe and syringe attachment(s) which enables a reliable and controlled aspiration maneuver, to test for the presence of blood indicating that a blood vessel has been penetrated, and other critical operations to be performed easily with one hand.

BRIEF DESCRIPTION OF THE DRAWING

These and further novel features of the present invention are better understood by taking the following Drawing figures together with the Detailed Description, wherein.

DETAILED DESCRIPTION

The embodiments according to the present invention include a generally tubular member (e.g. 110A-110C, 110F-110G) that substantially surround a finger or fingers inserted therein, and further include a tapered surface or surfaces (e.g. 122, 124, 140, 160, 222, 224) that diminish the cross section opening of the tubular member as you move along the length of the tubular member, or adjustable structures (e.g. 110D, 110E) that comprises structures (e.g. 178 and 190, 192) that adjust to more closely grip a finger inserted within the structures.

Figure 1:
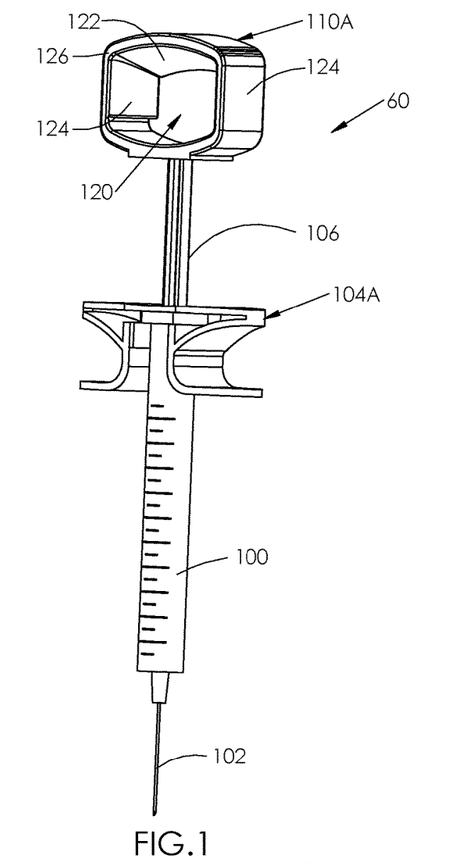
FIG. 1 is an isometric view of the syringe assembly of a first exemplary embodiment of the present invention.
Figure 2:
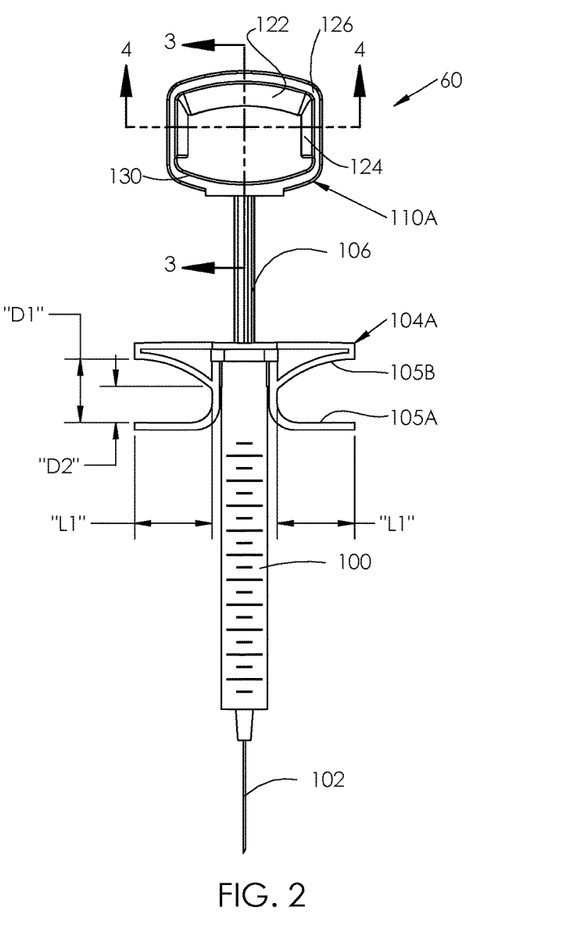
FIG. 2 is a front elevation view of the syringe assembly by the embodiment of FIG. 1.

As applied to a first exemplary embodiment 60 of FIGS. 1-4, a plunger includes a plunger rod 106 ring structure 110A that is a finger receiver with a bottom portion 130 attached to plunger rod 106 end, and has a tapered upper and sides 122, 124 surfaces, wherein the tapered surfaces of the ring 110A accommodate, snag or otherwise engage different sizes of fingers. The syringe barrel 100 includes finger grips 104A that have a sloped surface proximal to said plunger rod 106 facing an opposite finger grip, with diminishing internal clearance there between (e.g. moving from distance D1 to D2 shown in FIG. 2) for distances closer to the syringe barrel 100. In this embodiment, the taper of the proximal surface is mildly arcuate, as shown in FIGS. 1, 2 and in later figures. The needle 102 is connected to the barrel 100 at an end distal to the end from which the plunger rod 106 emerges, and the needle 102 receives the material within the barrel 100 as the plunger rod 106 is advanced into the barrel 100.

Figure 3:
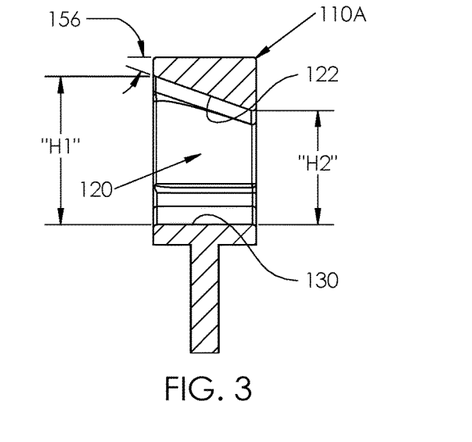
FIG. 3 is a section 3-3 of the embodiment of FIG. 2.
Figure 4:
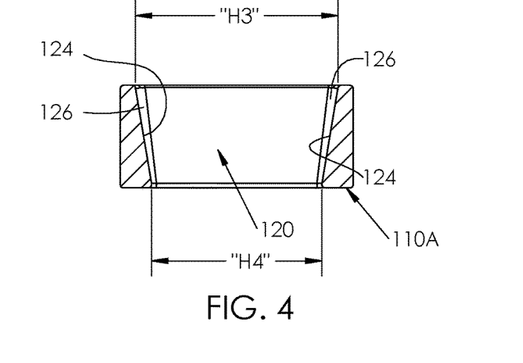
FIG. 4 is a section 4-4 of the embodiment of FIG. 2.

As shown on cross-sections FIG. 3 and FIG. 4, the upper portion 122 of the ring structure 110A includes a tapered inside the ring surface of 122 and 124, and this taper at an angle 156 is selected to allow internal dimensions "H1" and "H2" in which to receive a finger. Dimension "H1" is larger than dimension "H2" and each taper may extend over the length of the ring 110A, and this allowed fingers with different size to be inserted into the ring, and the inward-facing ring tapered surface will accommodate to the finger size in vertical direction. This will restrict finger movement inside the ring in vertical direction.

Additionally, the ring by this embodiment includes a tapered surface 124 in horizontal direction (optionally separated by a recess 126 from the tapered surface 122) and these tapers provide the opening 120 inner dimensions "H3" and "H4". This horizontal taper will accommodate the finger horizontal size.

According to human hand scale (see link https://ultra-xeondotcom.wordpress.com/2016/02/25/human-scale-from-henry-dreyfuss/), thumb finger thickness (vertical dimensions) minimum dimensions for men are typically 17 mm and for women 15 mm with a typical maximum dimensions for men 24 mm and for women 19 mm.

Figures 5, 7:
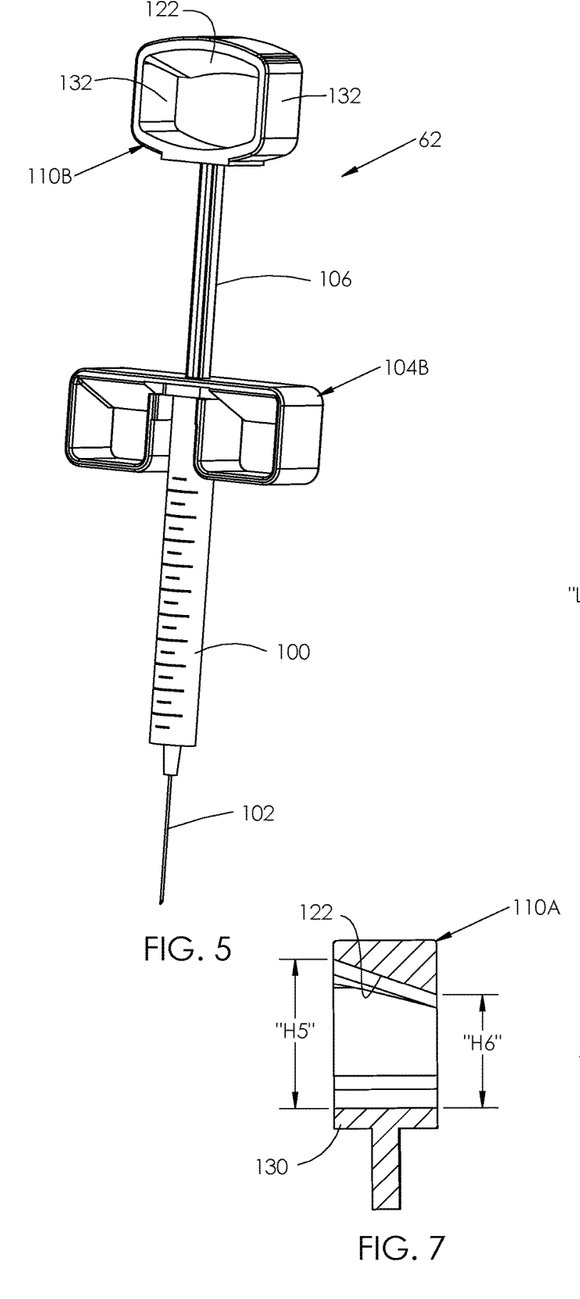
FIG. 5 is an isometric view of a syringe assembly by a second exemplary embodiment of the present invention.
FIG. 7 is a section 7-7 of the embodiment of FIG. 6.
Figures 15, 17:
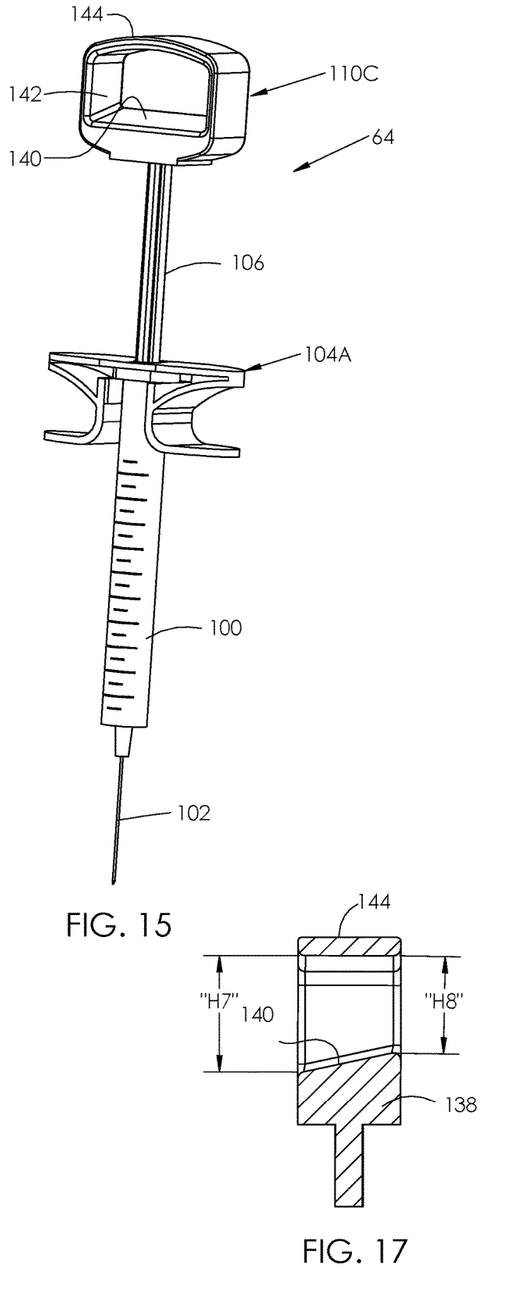
FIG. 15 shows an isometric view of a syringe assembly by a third exemplary embodiment of the present invention.
FIG. 17 shows a section 17-17 of the embodiment of FIG. 10.
Figure 16:
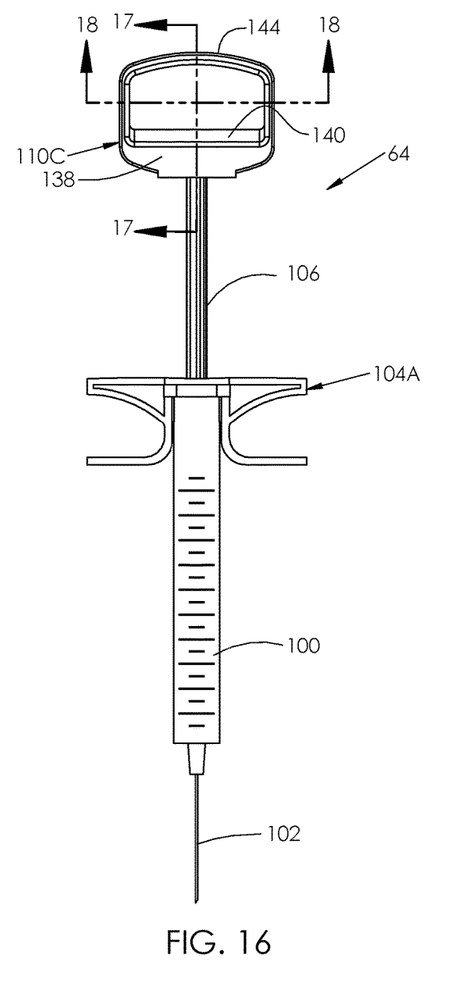
FIG. 16 shows a front elevation view of the syringe assembly by of the embodiment of FIG. 15.
Figure 18:
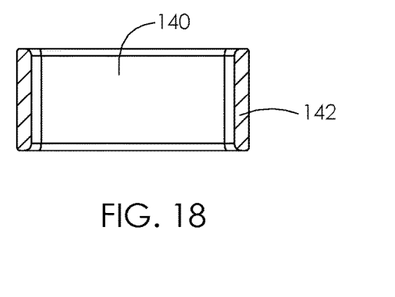
FIG. 18 shows a section 18-18 of the embodiment of FIG. 10.
Figure 45:
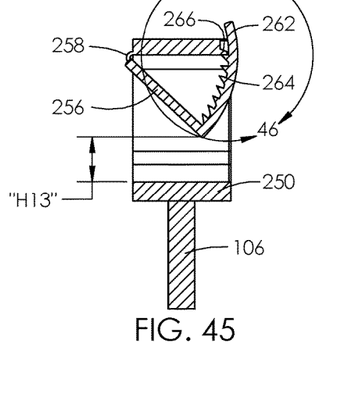
FIG. 45 is a section 45-45 of the embodiment of FIG. 43.

In the application drawings maximum vertical dimensions (finger entrance into the ring) represented by H1 (FIG. 1), H5 (FIG. 7), H7 (FIG. 17), H9 (FIG. 20), H11 (FIG. 26) and H14 (FIG. 50) and preferably this dimension should be slightly larger than 24 mm (typical maximum dimension for men). In the application drawings minimum vertical dimensions represented by H2 (FIG. 3), H6 (FIG. 7), H8 (FIG. 17), H10 (FIG. 21), H12 (FIG. 29) and H13 (FIG. 45) and preferably these dimensions should be slightly larger than 15 mm (minimum dimension for women). This combination of ring (e.g. 122, etc.), inside vertical taper (e.g. 124, etc.) dimensions, allowed adapt (snag) to the majority thumb finger size to comfortably perform the proximal (aspirating) stroke.

As result those tapered surfaces inside ring structure will restrict finger motions inside the ring 110A, allowing controlled injecting and aspiration stroke without having a gap (free finger movement) inside of the ring, because plunger will follow finger movement simultaneously.

Figure 11:
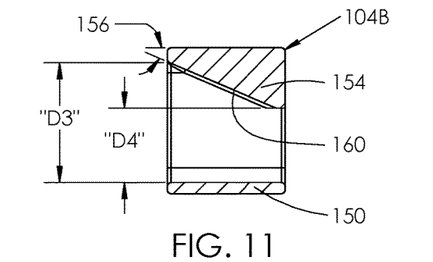
FIG. 11 shows sectional view 11-11 of the embodiment of FIG. 6.
Figure 12:
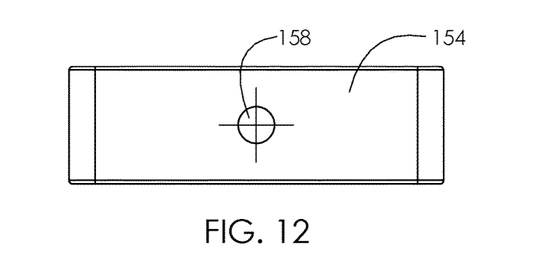
FIG. 12, FIG. 13 and FIG. 14 shows a top, and side and front elevation views of barrel finger holding attachment of the embodiment of FIG. 9.
Figure 13:
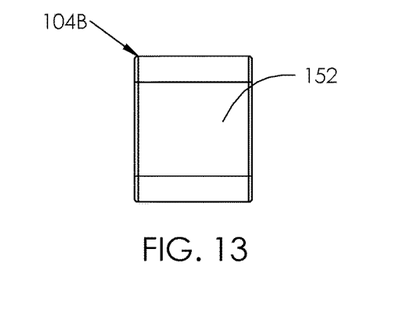

In another novel feature of the embodiment 60 having the syringe barrel 100 that includes an open structure finger grip 104A, that receives an index and middle finger for holding a barrel typically on to two portions on either side of the barrel 100. To minimize a vertical movement of those fingers during an aspiration (withdrawal) stroke without having a gap this barrel holding structure has an inside tapered shape indicated by dimensions "D1" and "D2" (Fig. 2) and "D3" and "D4" (FIG. 11). According to human hand scale (see above link), maximum index and middle finger thickness for men is typically 19 mm and minimum typically is 13 mm, and the typical maximum index and middle finger thickness for women is 16 mm and minimum is 11 mm, and the maximum width (horizontal dimensions) for men's index finger is 21 mm and for women is 18 mm and smallest width accordantly for men 15 mm and for women 13 mm. For middle finger for men the maximum is 21 mm and for women 18 mm and minimum width for men 15 mm and for women 13 mm. In most cases barrel finger grips (104A and 104B) will hold by the index and middle fingers.

According to this data, in the embodiments of FIGS. 1-4, the finger entrance 120 into the barrel finger holder structure (dimensions "D1" and "D3") should be slightly larger than 19 mm and smallest dimensions ("D2" and "D4") should be around 11 mm and the open loop finger grip (104A) dimension "L1" see FIG. 2 to have reliable finger gripping (or 'snag') should be more than half of maximum index and middle fingers width. In this case it should be more than 11 mm (21 mm max). By entering a finger within spacing D1, the substantially planar member 105A attached to and extending away from the barrel and closer to the needle 102 end of the barrel 100 in this exemplary embodiment together with the facing member 105B also attached to and extending away from the barrel, that includes a mildly curved taper (to more completely engage a somewhat oval finger) providing a diminishing spacing relative the planar member 105A that grips a finger inserted between members 105A and 105B as a finger (or fingers on opposing sides of the barrel 100), provide increased force on the inserted finger and corresponding increased gripping of the barrel 100. This taper design adapts to (snags) the majority of index and middle fingers size to comfortably perform the retracting (aspirating) stroke.

Figure 6:
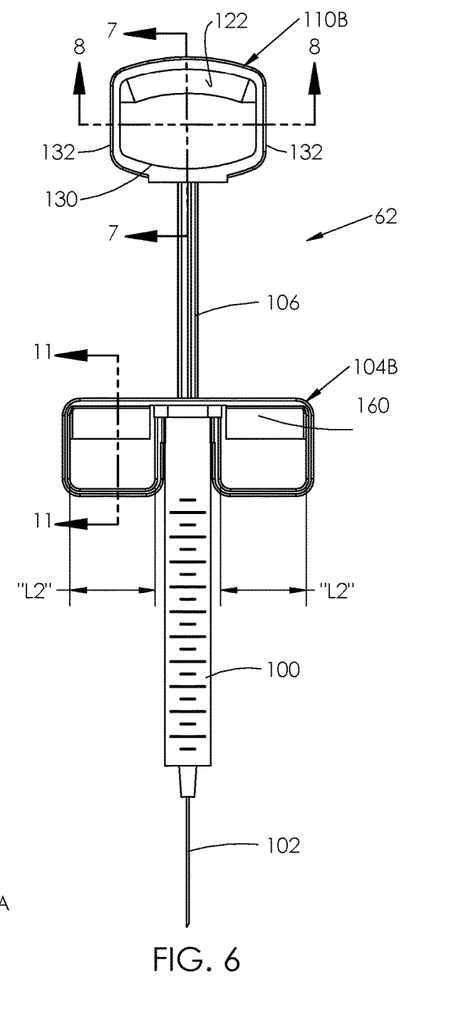
FIG. 6 is a front elevation view of the syringe assembly by the embodiment of FIG. 2.
Figure 8:
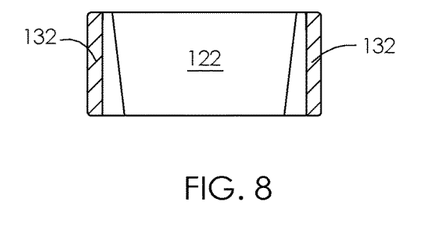
FIG. 8 is a section 8-8 of the embodiment of FIG. 6.

In case of close loop finger grips (104B, discussed below) dimension "L2" of FIG. 6, should be larger than maximum width of index and middle fingers, to allow finger to be inserted into the grip. I this case it should be larger than 21 mm.

Figure 9:
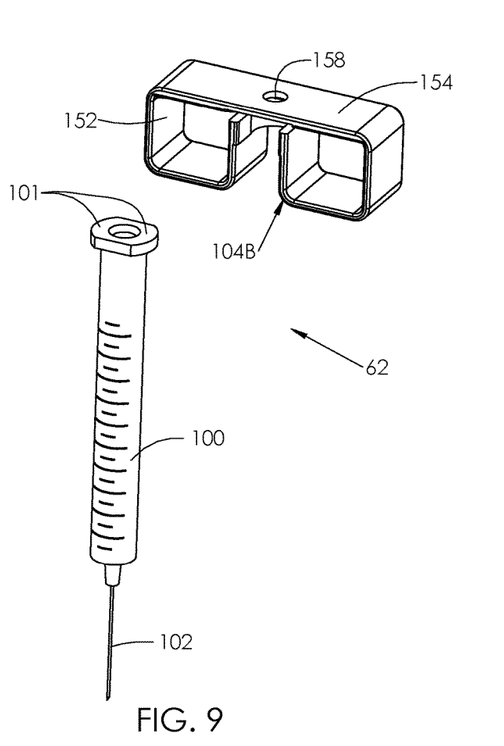
FIG. 9 is an exploded view of syringe a barrel and finger holding attachment embodiment.
Figure 10:
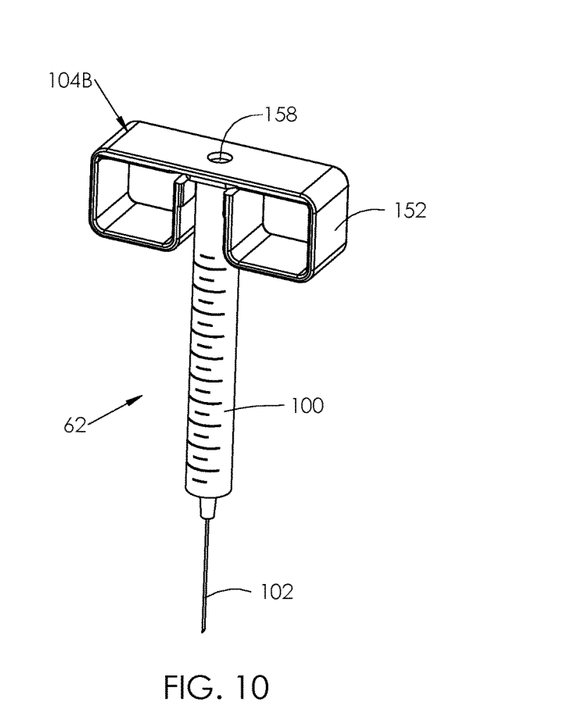
FIG. 10 shows an isometric view of a syringe barrel and finger holding attachment assembly.
Figure 14:
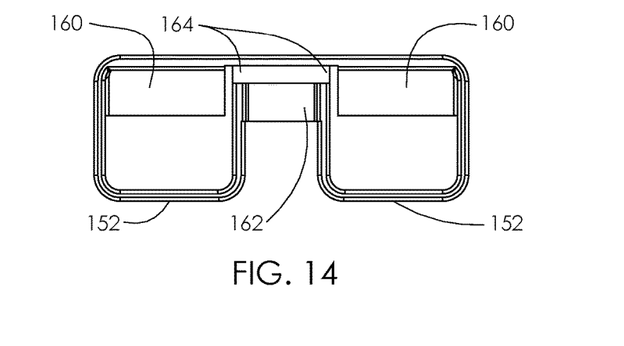

In another novel feature of the further embodiment 62 having the syringe barrel 100 that includes, or receives an optionally removable from, a closed short squared tubular finger grip 104B, that separately receives an index and middle finger for holding the barrel 100. In the embodiments 62 of FIGS. 5 and 6, finger grip 104B is shown seated on, or part of the barrel 100, while the embodiments of FIGS. 9, 10 show the finger grip 104B separate from the barrel 100 but is capable of being seated on the barrel shoulder or collar 101 within a recess 164 (FIG. 14) formed by a ring segment 162 that surrounds the barrel 100 and forms the recess 164 relative to the top of the finger grip 104B.

The finger grip 104B includes two finger grip sections disposed on opposite sides of the barrel 100, and each section includes an internal surface 160 inclined at an angle 156 relative to the top 154 of the finger grip to provide an internal opening that tapers from an opening dimension D3 to D4 along the width of the of the finger grip sections. As the plunger is advanced into the barrel 100, the operator finger engages (applies force) on to the surfaces 160. The finger grip 104B bottom of 152 is disposed to provide openings according to the criteria described above in regard to the embodiments of FIGS. 1-4. The top 154 of the finger grip 104B includes an opening 158 though the plunger extends when the finger grip 104B is seated on the barrel 100. The dimensions D3, D4 of Fig.11 are equivalent to the dimensions H3, H4 shown in Fig.3.

A further embodiment 64 is shown in FIGS. 15-18, wherein the plunger 100 finger grip ring 110C includes a slightly curved upper portion 144 attached to a bottom portion 138 by sides 142 typically having uniform thickness (but adaptable to be tapered as shown in Fig.4 in other embodiments), wherein the bottom portion 144 includes a tapered surface 140, analogous to the tapered portion 122 of FIGS. 1-7, but applied to the ring 110C proximal to the plunger rod 106. The opening heights H7 and H8 correspond to finger entrance and exit of other embodiments herein.

Figure 19:
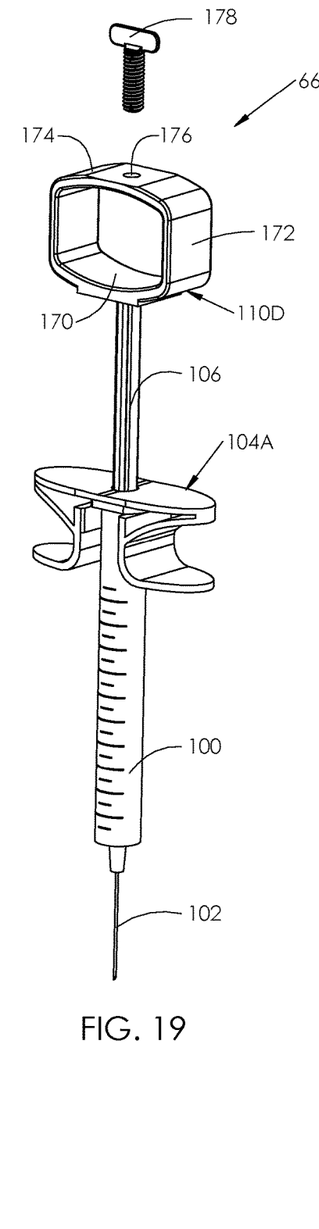
FIG. 19 shows an exploded isometric view of a syringe assembly by a fourth exemplary embodiment of the present invention.
Figure 20:
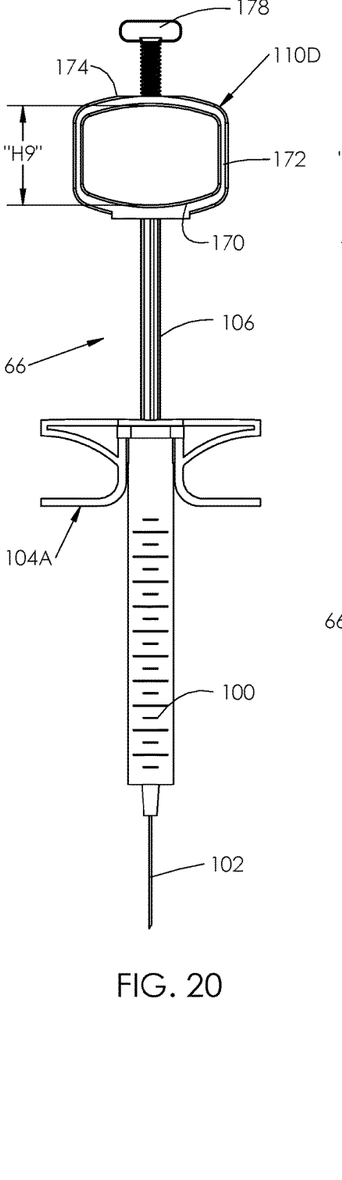
FIG. 20 and FIG. 21 are front elevation view of the syringe assembly by the embodiment of FIG. 19 of the present invention showing different screw 178 positions.
Figure 21:
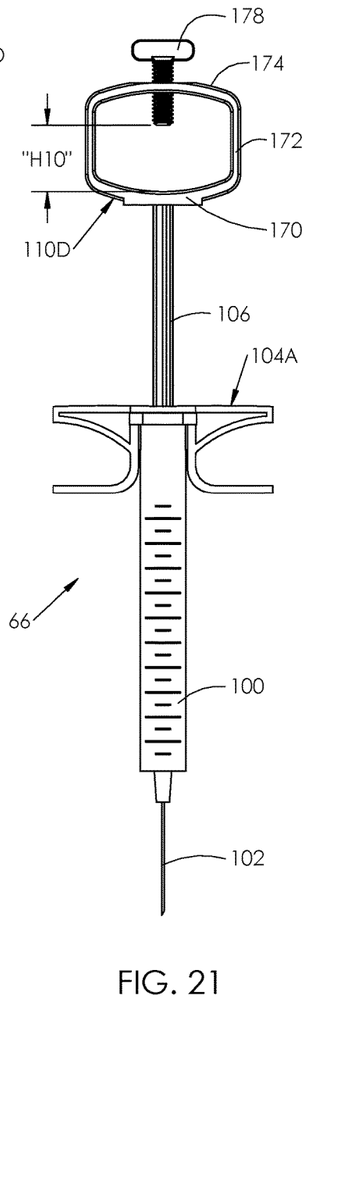
Figure 22:
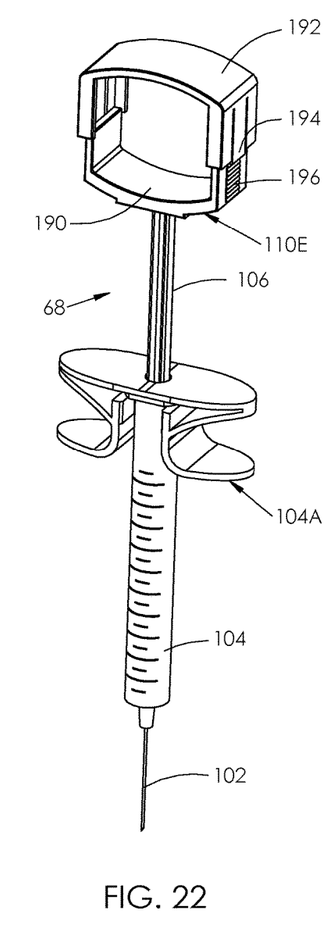
FIG. 22 shows an isometric view of a syringe assembly by a fifth exemplary embodiment of the present invention.
Figure 23:
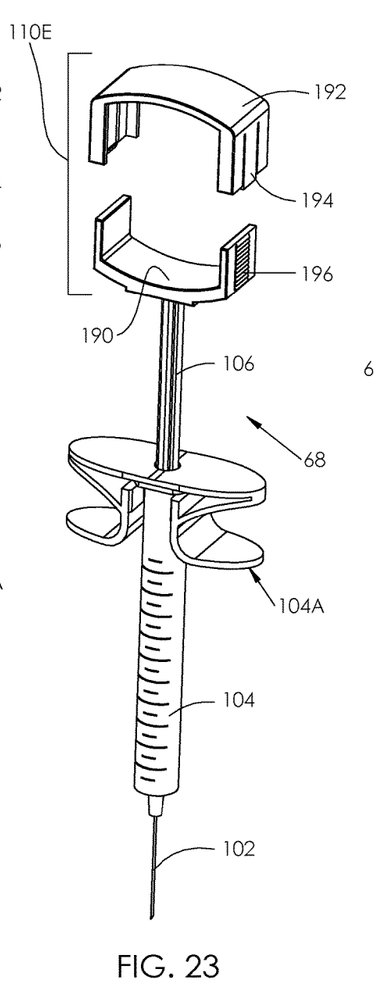
FIG. 23 shows an exploded isometric view of the syringe assembly by a the embodiment of FIG. 22.
Figure 24:
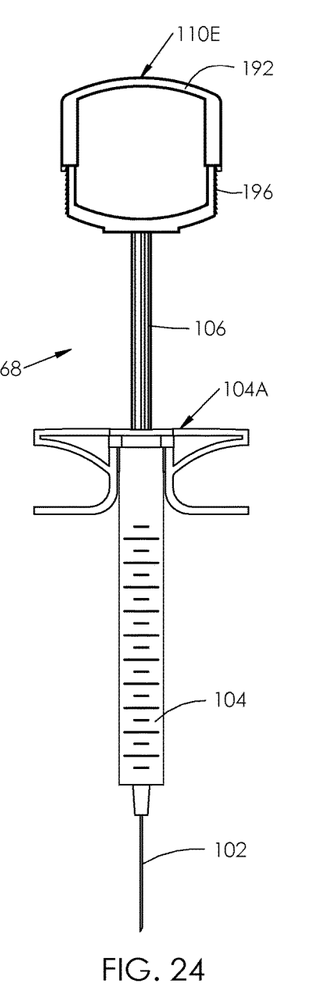
FIG. 24 shows a front elevation view of the syringe assembly of the embodiment of FIG. 22.

A fourth embodiment 66 is shown in FIGS. 19-21, wherein the plunger 106 ring 110D comprises a closed annular structure having substantially (but not necessarily) uniform side wall thickness including walls 172 proximal to the sides of fingers inserted therein, a slightly (but not necessarily) curved bottom 170 and curved top 174 having a spacing H9 and a threaded aperture 176 in the curved top 174 that receives a corresponding threaded screw 178 that may be advance (e.g. distance H10) into the ring 110D to secure or limit movement of a finger inserted therein. Finger grips 104A, attached to the barrel 100, are also included in this embodiment.

A fifth embodiment 68 is shown in FIGS. 22-36 comprising a two-part ring 110E including a bottom part attached to the plunger rod 106 and having at least one toothed surface 196, and an upper part 192 which overlays and/or engages the lower part 190 and has a toothed finger 194 having a pawl 204 that engages the toothed surface 196 that together work to allow the ring 110E upper and lower portions to be moved together to decrease the space (that receives a finger) by compression pressure on the ring 110E and restrict increasing the space from a ring 110E upper and lower part separating force. Finger grips 104A, attached to the barrel 100, are also included in this embodiment.

Figures 25, 26, 27, 28, 29, 30, 31, 32, 33, 34, 35, 36:
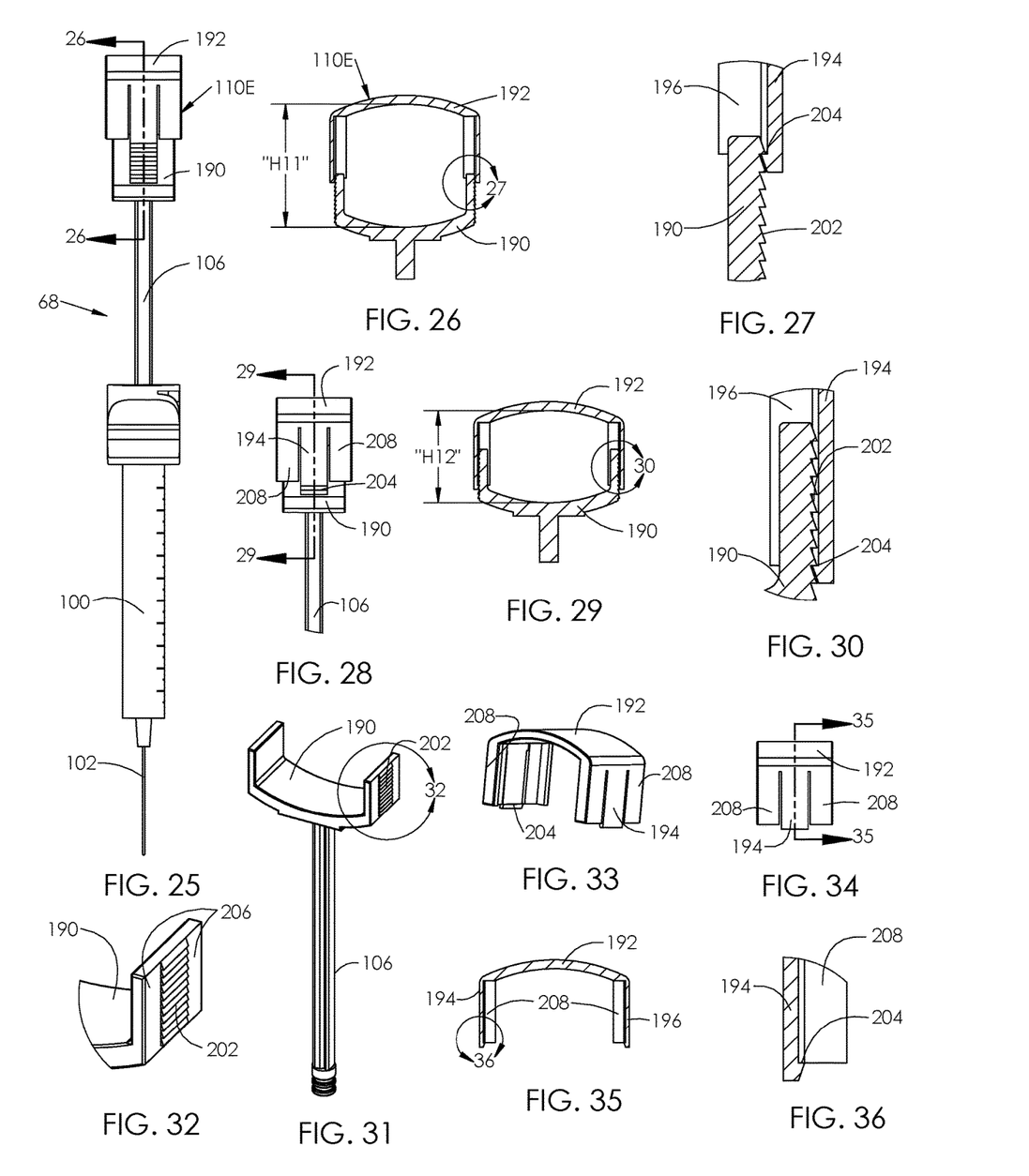
FIG. 25 shows a side elevation view of the syringe assembly of the embodiment of FIG. 22, when the upper ring portion is in a top position
FIG. 26 shows a section 26-26 of the embodiment of FIG. 25.
FIG. 27 is an enlarged view 27 of the embodiment of FIG. 26.
FIG. 28 shows a partially side view of the syringe assembly of the embodiment of FIG. 22, when the upper ring portion is in a bottom position.
FIG. 29 shows a section 29-29 of the embodiment of FIG. 28.
FIG. 30 is an enlarged view 30-30 of the embodiment of FIG. 29.
FIG. 31 is isometric view of the plunger with ring bottom portion of the embodiment of FIG. 22.
FIG. 32 is an enlarged view 32 of the embodiment of FIG. 31.
FIG. 33 is an isometric view of the ring upper portion of the embodiment of FIG. 22.
FIG. 34 is a side elevation view of ring upper portion of the embodiment of FIG. 22.
FIG. 35 is a section 35-35 of the embodiment of FIG. 34.
FIG. 36 is an enlarged view 36 of the embodiment of FIG. 35.
Figure 37:
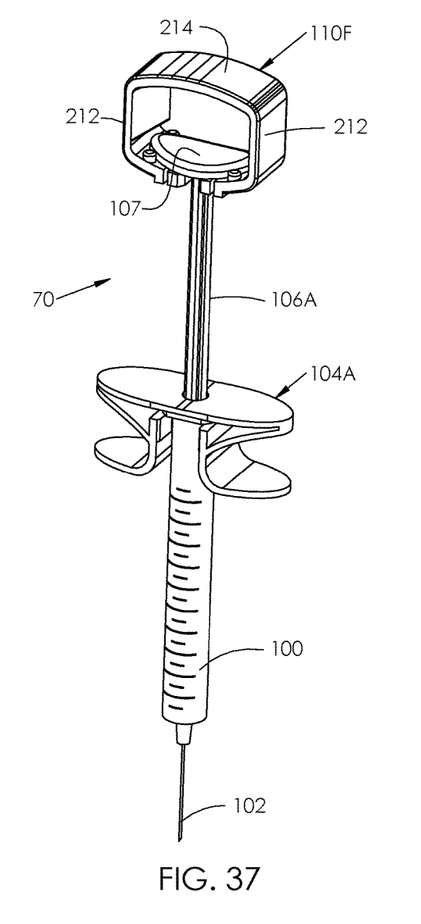
FIG. 37 shows an isometric view of a syringe assembly by a sixth exemplary embodiment of the present invention.
Figure 38:
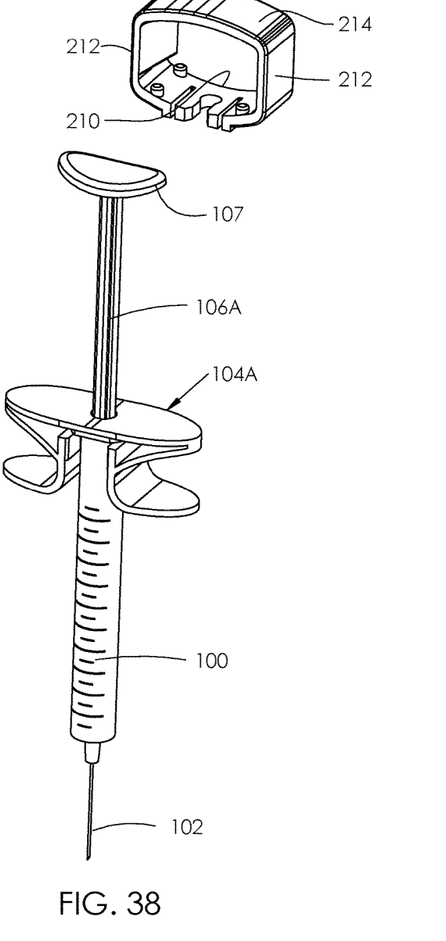
FIG. 38 shows an exploded isometric view of syringe assembly by the embodiment of FIG. 37.
Figure 39:
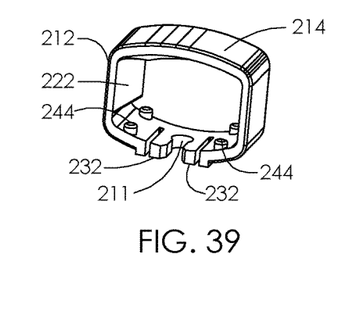
FIG. 39 shows an isometric view of an attachable ring embodiment of the present invention.
Figure 40:
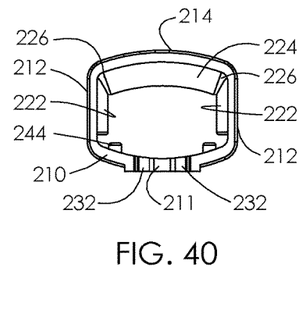
FIG. 40 is a front elevation view of the attachable ring of the embodiment of FIG. 39.
Figure 41:
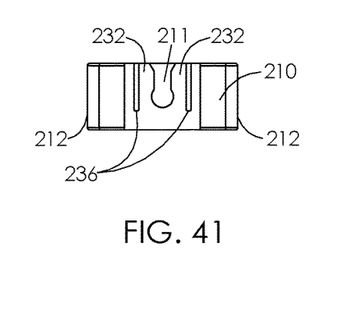
FIG. 41 is a bottom view of the attachable ring of the embodiment of FIG. 39.

A vertical cross-section 26 of the embodiment 68 shown in FIG. 25 is shown in FIG. 26, wherein the maximum vertical finger opening H11 between curved portions 190 and 192 is shown with the portions engaged and secured by toothed surface 202 and pawl 204, shown in enlarged detail in FIG. 27. A minimum finger distance H12 is shown in FIG. 29 as the cross-section of FIG. 28, wherein the upper and lower portions 192, 190 are substantially completely engaged, and the engaged detail is shown in FIG. 30 wherein the pawl tooth 204 engages the end of the toothed surface proximal the bottom of portion 190.

Smooth surfaces 206 adjacent the toothed surface 202 on bottom piece 190 are shown in the enlarged portion FIG. 32 of FIG. 31, which receive smooth surfaces of members 208 of upper piece 192 as shown in FIGS. 33, 34. The finger 194 is separated from and parallel to smooth surface members 208 to allow pawl 204 to engage the toothed surface 202 without being restricted by the smooth surface members 208. Members 208 may also comprise an "L" shaped cross-section to engage the edges of the lower portion 190. A further view of only the upper portion 192 of ring 110E is show in FIG. 35 and detail FIG. 36, wherein the point of the pawl 204 is substantially at the end of the side of the "L" shaped member 208.

A sixth embodiment 70 is shown in FIGS. 37-41 having a removable plunger finger ring 110F which engages and is retained on a standard plunger rod 106A or custom plunger. As shown in more detail in FIGS. 39-41, the ring 110F typically (but not necessarily) comprises a continuous and substantially uniform wall thickness ring having top 214, sides 212, and bottom 210, wherein the bottom includes inward-extending locating protrusions 244 that laterally engage the plunger rod 106A handle 107 when the handle is seated within aperture 211 between prongs 232 (or other retaining devices) to reduce relative motion therebetween upon application of force to the ring 110F by a finger. To permit resilient grasping of the plunger rod 106A, the prongs 232 are partially separated by spaces 236 from the bottom 210. The side walls 212 and top 214 may also include tapered surfaces 222, 224, with or without spaces 226, analogous to the tapered surfaces and walls of other embodiments shown herein.

Figure 42:
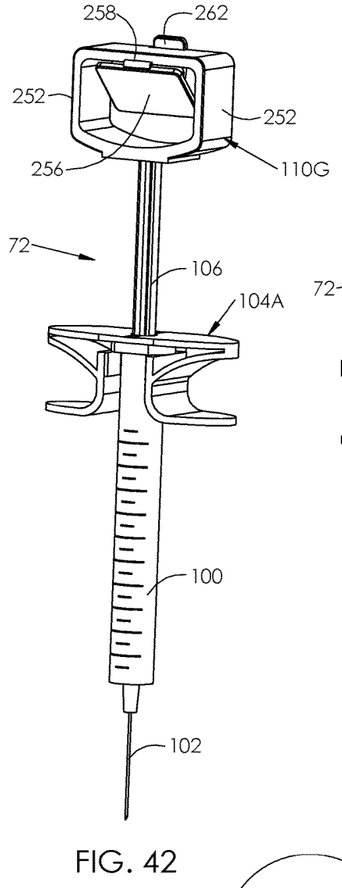
FIG. 42 is an isometric view of syringe assembly by a seventh exemplary embodiment of the present invention.
Figure 43:
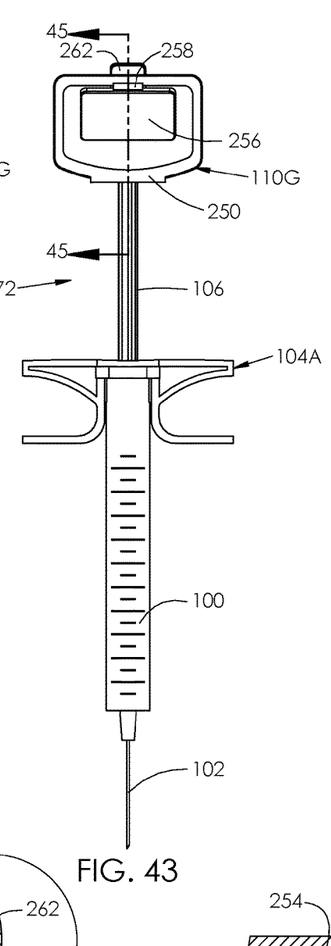
FIG. 43 and FIG. 44 is a front and side elevation view respectively, of syringe assembly by embodiment of FIG. 42.
Figure 44:
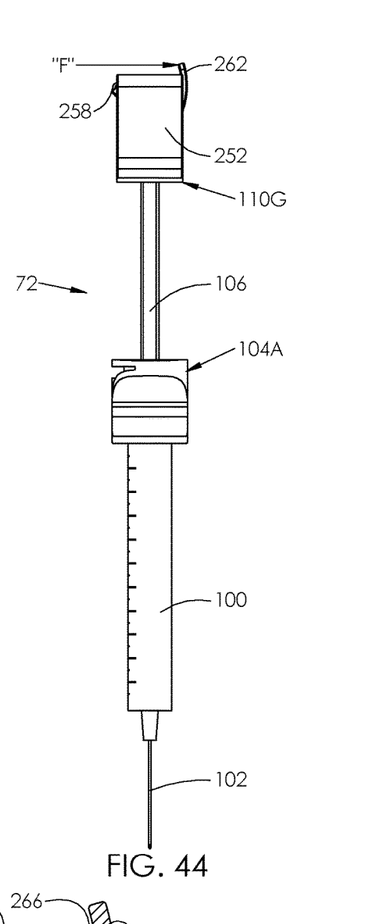
Figure 46:
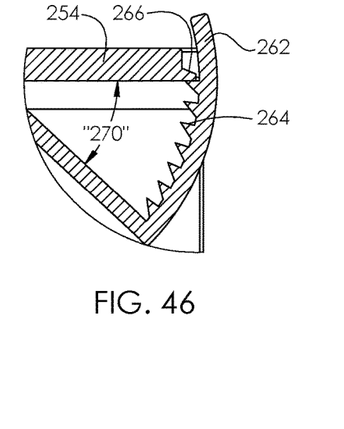
FIG. 46 is an enlarged view 46 of the embodiment of FIG. 45.

A seventh embodiment 72 is shown in FIGS. 42-55, wherein an isometric view of syringe assembly is shown in FIG. 42, front and side elevation views of FIGS. 43 and 44, and includes the barrel 100 and attached needle, with plunger rod 106 and finger grips 104A (or 104B), and thumb/finger ring 110G includes a finger plate 256 attached by a hinge 258 and toothed latch (FIG. 46) that is movable to secure the finger plate 256 into position to establish a minimum distance "H13" (as shown on FIG. 45) to secure a "small" thumb finger by moving the finger holding plate downward to an angle 270 (FIG. 46). An isometric view of syringe assembly by the seventh embodiment initially allows thumb finger holding plate in position to establish an open internal opening distance "H14" (as shown on FIG. 50) to secure a "larger" thumb finger and is adjustable to an even larger opening as desired.

In this embodiment as shown in FIGS. 42-46, the thumb/finger plate 256 includes an arcuate member 262 having a radius center substantially at the location of the hinge 258, and includes sawtooth-shaped teeth 264 on a surface facing the hinge 258, and engaging a narrowed edge 266 of the top portion 254 of the thumb/finger ring 110G. A bottom 250 is connected to the end of the plunger rod 106, and is also connected to the top portion 254 wall by opposing side walls 252 to form an annular member. To reduce the internal space, a downward (e.g. toward the needle 102) force or force generally perpendicular to the plane of the top portion 254 narrowed edge is applied allowing the incline of the tooth to slip past the narrowed edge 266 and latch the finger/plate 256 into the next reduced internal space position to allow reducing the internal space, e.g. H13.

Figures 47, 48, 49, 50, 51:
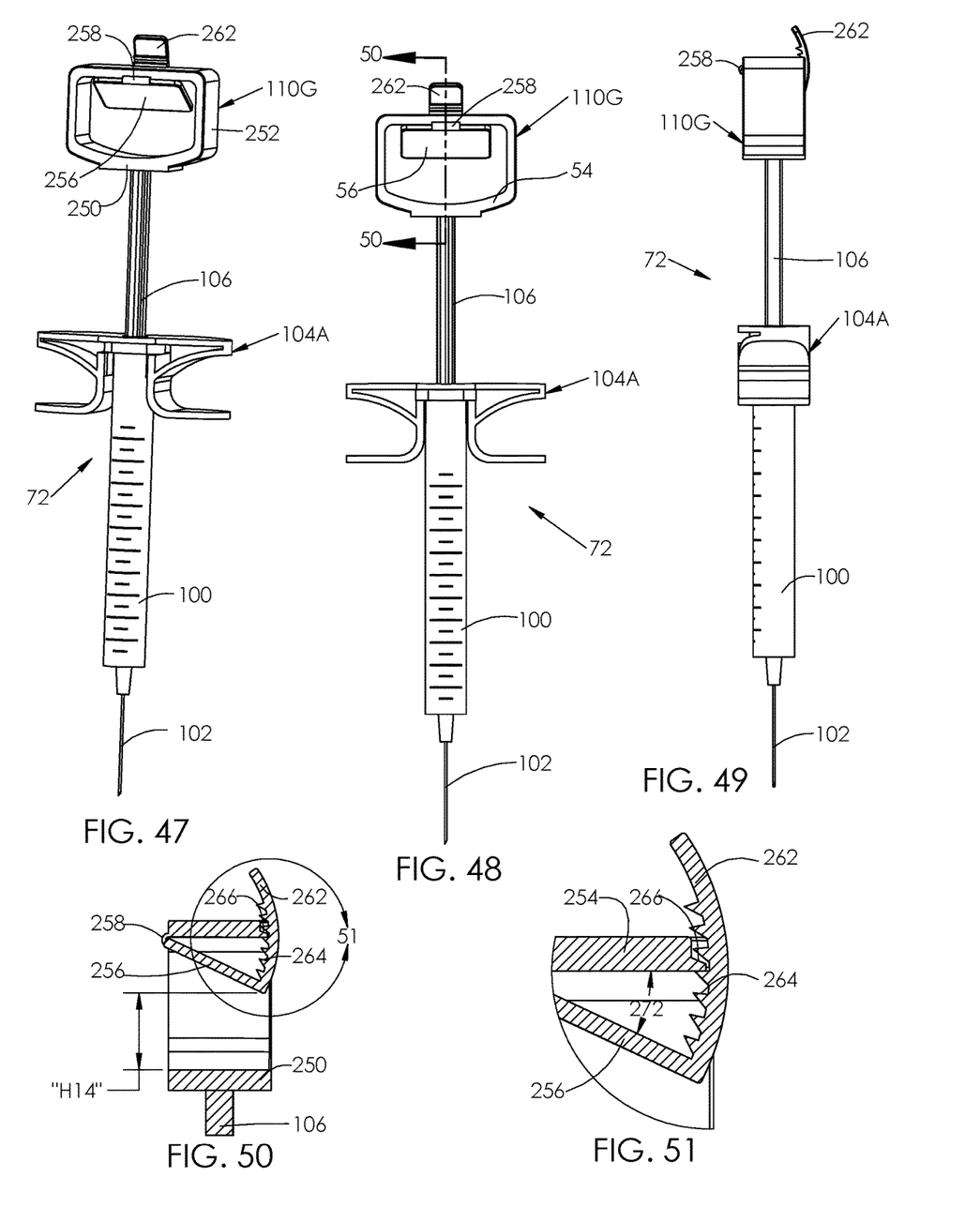
FIG. 47 is an isometric view of syringe assembly of the embodiment of FIG. 42.
FIG. 48 and FIG. 49 are front and side elevation views of syringe assembly of the embodiment of FIG. 42.
FIG. 50 is a section 50-50 of the embodiment of FIG. 48.
FIG. 51 is an enlarged view 51 of the embodiment of FIG. 50.

The isometric, and front and side elevation views of FIGS. 47-49 illustrate raising or retracting the finger plate 256 to increase the ring 110G internal opening, wherein the arcuate member 262 having teeth 266 of the arcuate member 262 is moved away from engaging the edge 266 by a force F (FIG. 44) on the arcuate member 262 free end generally away from the hinge 258 and a compressing force (upward in the views of FIGS. 47-49) is applied to allow increasing the internal space, e.g. H14. An enlarged view is shown in FIG. 50 showing the engaging of the narrowed edge 266 of the ring 110G top portion 254 engaging a middle range of the arcuate member 262 teeth 264. A further enlargement is shown in FIG. 51 including angle 272 that is less than angle 270 of FIG. 46.

Figure 52:
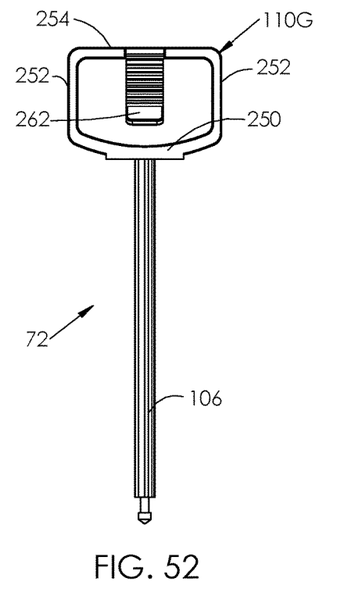
FIG. 52, FIGS. 53 and 54 are front and side elevation, and top views respectively, of the plunger of the embodiment of FIG. 42.
Figures 53, 54:
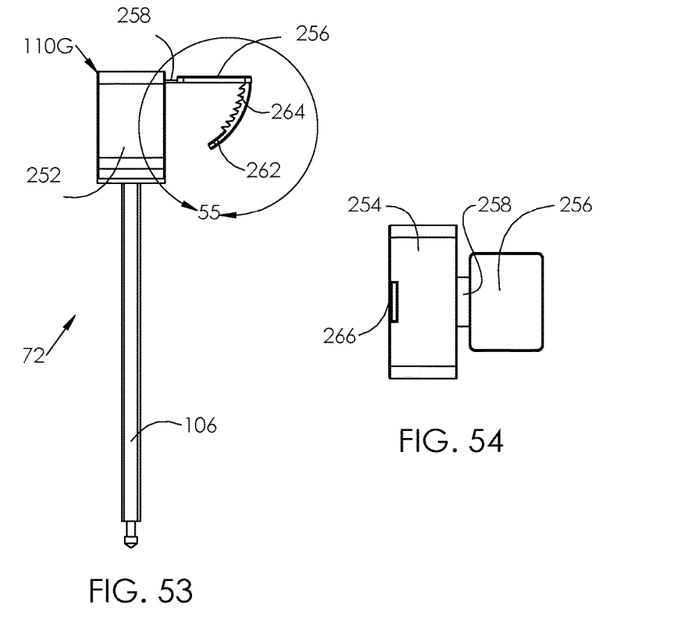
Figure 55:
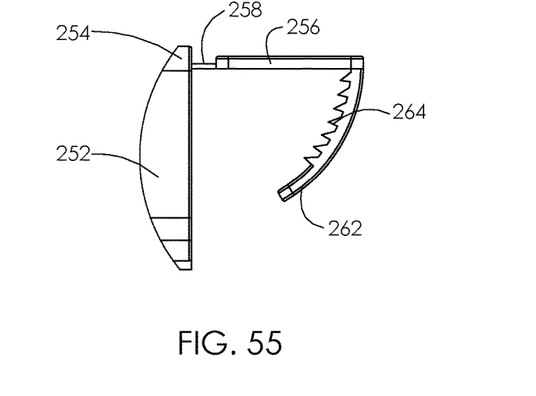
FIG. 55 is an enlarged view 55 of the embodiment of FIG. 53.

The front, side elevation, and top plan views of plunger rod 106 with thumb/finger ring 110G of this embodiment is shown in FIGS. 52-54 as a single piece fabricated by injection molding. In this embodiment, the plunger rod 106, thumb/finger ring 110G, 'live' (bendable from mold material) hinge 258 attached to thumb/finger ring 110G, finger plate 256, and arcuate member 264 comprise a single mold material or molded structure. After molding and release from the mold (not shown), the finger plate 256 and arcuate member 262 is directed through the ring 110F interior opening, and allow teeth 264 to engage the narrowed edge 266 on top portion 253 at the desired angle, e.g. 270, 272, or otherwise.

Modification and substitutions by one of ordinary skill in the art are within the scope of the present invention, which is not limited except by the claims that follow.

What is claimed is:

1. A syringe having improved control members, comprising:
   a barrel having a region therein to retain material, and a first opening at one end through which said material is dispensed, and a second opening distal from said first opening;
   a plunger including
      a plunger rod disposed to enter said barrel through said second opening and extending into said barrel, and having a plunger rod first end within said barrel and a plunger rod second end external to said barrel, and having an axis of motion within said barrel; and
      a finger receiver connected to said plunger rod second end, and comprising an annular member having a wall defining an opening having an opening length extending in a dimension substantially perpendicular to said plunger rod axis of motion, wherein a finger plate extends toward said finger receiver opening and is adjustably inclined over said opening length thus providing a selectively diminished finger receiver opening over said opening length.

2. The syringe of claim 1, further including a barrel finger grip attached to said barrel having two surfaces extending away from said barrel in the same direction and having a minimum spacing therebetween proximal to said barrel, and increasing spacing therebetween at distances distal from said barrel.

* * * * *